US012636326B2

(12) United States Patent
Zhao et al.

(10) Patent No.: US 12,636,326 B2
(45) Date of Patent: May 26, 2026

(54) *LACTOBACILLUS* SP. BB1 ENHANCING MEMORY ABILITY, FERMENTED FOOD AND APPLICATION THEREOF

(71) Applicant: Jiangnan University, Wuxi (CN)

(72) Inventors: Wei Zhao, Wuxi (CN); Li Li, Wuxi (CN); Zhaoyang Qi, Wuxi (CN)

(73) Assignee: Jiangnan University, Wuxi (CN)

( * ) Notice: Subject to any disclaimer, the term of this patent is extended or adjusted under 35 U.S.C. 154(b) by 404 days.

(21) Appl. No.: 17/902,937

(22) Filed: Sep. 5, 2022

(65) Prior Publication Data

US 2023/0027537 A1 Jan. 26, 2023

Related U.S. Application Data

(63) Continuation of application No. PCT/CN2022/071740, filed on Jan. 13, 2022.

(30) Foreign Application Priority Data

Apr. 10, 2021 (CN) .......................... 202110388257.9

(51) Int. Cl.
A23C 9/123 (2006.01)
A23L 33/135 (2016.01)
A61K 35/747 (2015.01)

(52) U.S. Cl.
CPC .......... *A61K 35/747* (2013.01); *A23L 33/135* (2016.08)

(58) Field of Classification Search
None
See application file for complete search history.

(56) References Cited

U.S. PATENT DOCUMENTS

2018/0355445 A1* 12/2018 Kim ..................... A61K 35/747

FOREIGN PATENT DOCUMENTS

| CN | 101067119 A | 11/2007 | |
|---|---|---|---|
| CN | 101325960 A | 12/2008 | |
| CN | 108603162 A | 9/2018 | |
| CN | 111465684 A | 7/2020 | |
| CN | 113122473 A | 7/2021 | |
| EP | 2676671 A1 * | 12/2013 | ........... A23L 33/105 |
| WO | WO-2019081577 A1 * | 5/2019 | ......... A23C 19/0323 |

(Continued)

OTHER PUBLICATIONS

Song et al. "Recent application of probiotics in food and agricultural science." Probiotics 10.1 (2012): 1-34 (Year: 2012).*

(Continued)

*Primary Examiner* — Thane Underdahl
*Assistant Examiner* — Mary A Crum
(74) *Attorney, Agent, or Firm* — IPro, PLLC; Na Xu

(57) ABSTRACT

The disclosure discloses *Lactobacillus* sp. BB1 enhancing memory ability, a fermented food and application thereof, and belongs to the technical field of microorganisms. The *Lactobacillus* sp. BB1 disclosed by the disclosure can be used for preparing functional foods, health-care products and drugs that enhance the memory ability of a healthy individual and improve memory impairment. The disclosure further provides the fermented food. The fermented food is prepared by fermentation with *Lactobacillus* sp. BB1, comprises a solid food, a liquid food and a semisolid food, and has a wide application prospect.

6 Claims, 5 Drawing Sheets

Specification includes a Sequence Listing.

(56) References Cited

FOREIGN PATENT DOCUMENTS

WO        2019169181  A1      9/2019

OTHER PUBLICATIONS

Milky Day blog, How to make low fat milk, 2025, milkyday.com/blog/2018/09/15/how-to-make-low-fat-milk/) (Year: 2025).*
Aidoo, et al. "Industrial manufacture of sugar-free chocolates—Applicability of alternative sweeteners and carbohydrate polymers as raw materials in product development." Trends in Food Science & Technology 32.2 (2013): 84-96 (Year: 2013).*
Zelman, What's the difference between sucrose and fructose, 2024, webmd.com/diet/whats-the-difference-between-sucrose-and-fructose (Year: 2024).*
HM046568 (Genbank HM046568, Uncultured *Lactobacillus* sp. clone AMD_E5 16S ribosomal RNA gene, partial sequence, ncbi.nlm.nih.gov/nuccore/HM046568.1) (Year: 2011).*

* cited by examiner

SEQUENCE LISTING

```
Sequence total quantity: 12
SEQ ID NO: 1            moltype = DNA  length = 20
FEATURE                 Location/Qualifiers
source                  1..20
                        mol_type = other DNA
                        organism = synthetic construct
SEQUENCE: 1
tgacgcagat tatgtttgaa                                          20

SEQ ID NO: 2            moltype = DNA  length = 21
```

-continued

```
FEATURE              Location/Qualifiers
source               1..21
                     mol_type = other DNA
                     organism = synthetic construct
SEQUENCE: 2
agcgtatagc gaaagtacag c                                                    21

SEQ ID NO: 3         moltype = DNA   length = 20
FEATURE              Location/Qualifiers
source               1..20
                     mol_type = other DNA
                     organism = synthetic construct
SEQUENCE: 3
ggcattcaaa gatttgccgc                                                      20

SEQ ID NO: 4         moltype = DNA   length = 20
FEATURE              Location/Qualifiers
source               1..20
                     mol_type = other DNA
                     organism = synthetic construct
SEQUENCE: 4
gctgtgtttg ctcgcattga                                                      20

SEQ ID NO: 5         moltype = DNA   length = 20
FEATURE              Location/Qualifiers
source               1..20
                     mol_type = other DNA
                     organism = synthetic construct
SEQUENCE: 5
catccgctac cgccatactt                                                      20

SEQ ID NO: 6         moltype = DNA   length = 20
FEATURE              Location/Qualifiers
source               1..20
                     mol_type = other DNA
                     organism = synthetic construct
SEQUENCE: 6
cgtcgtccgg aatcctgtag                                                      20

SEQ ID NO: 7         moltype = DNA   length = 20
FEATURE              Location/Qualifiers
source               1..20
                     mol_type = other DNA
                     organism = synthetic construct
SEQUENCE: 7
aaacgggggga tgagatgtcg                                                     20

SEQ ID NO: 8         moltype = DNA   length = 22
FEATURE              Location/Qualifiers
source               1..22
                     mol_type = other DNA
                     organism = synthetic construct
SEQUENCE: 8
tcggaatctt ttcacctgag ct                                                   22

SEQ ID NO: 9         moltype = DNA   length = 21
FEATURE              Location/Qualifiers
source               1..21
                     mol_type = other DNA
                     organism = synthetic construct
SEQUENCE: 9
acctcgagac tccgaagatg t                                                    21

SEQ ID NO: 10        moltype = DNA   length = 20
FEATURE              Location/Qualifiers
source               1..20
                     mol_type = other DNA
                     organism = synthetic construct
SEQUENCE: 10
acgttgcacg gttgcatttc                                                      20

SEQ ID NO: 11        moltype = DNA   length = 22
FEATURE              Location/Qualifiers
source               1..22
                     mol_type = other DNA
                     organism = synthetic construct
SEQUENCE: 11
tcacagcgtt gaatgtaacc ac                                                   22
```

-continued

```
SEQ ID NO: 12          moltype = DNA   length = 20
FEATURE                Location/Qualifiers
source                 1..20
                       mol_type = other DNA
                       organism = synthetic construct
SEQUENCE: 12
tcagaatcgt gtacggtggc                                         20
```

LACTOBACILLUS SP. BB1 ENHANCING MEMORY ABILITY, FERMENTED FOOD AND APPLICATION THEREOF

REFERENCE TO SEQUENCE LISTING

The instant application contains a Sequence Listing in XML format as a file named "YGHY-2022-39.xml", created on Apr. 6, 2026, of 11676 bytes in size, and which is hereby incorporated by reference in its entirety.

TECHNICAL FIELD

The disclosure relates to *Lactobacillus* sp. BB1 enhancing memory ability, a fermented food and application thereof, and belongs to the technical field of microorganisms.

BACKGROUND

Learning and memory are the basis of human recognition and abilities requisite for individuals to adapt to social environment to live better. Many factors such as lack of sleep, pressure, aging and disease will cause decline of learning and memory ability, and severe learning and memory disorder not only affects life and social adaptability of individuals, but also brings heavy pressure and economical burden to family and society. At present, intelligence reinforcing functional products for improving the learning and memory ability of infants, youngsters, adults and old people are very limited in effect, and in particular, there are no effective treatment means for memory impairment caused by neurodegenerative diseases such as senile dementia.

An intestinal flora called an "internalized external environment" takes part in various physiological activities such as digestion, metabolism and immunization of a host. A gut-brain axis is a bidirectional information exchange system between the intestinal flora and a brain, and the intestinal flora may affect the cerebral function and behaviors of the host through the gut-brain axis. Disorder of the intestinal flora is closely related to various central nervous system diseases such as Parkinson's disease, Alzheimer's disease and depressive disorder. More and more researches have found that hypomnesia or memory impairment caused by aging or diseases is related to imbalance of the intestinal flora of the host. Flora imbalance of a sterile rat and an antibiotic-treated rat will cause decline of working memory ability and spatial memory ability. Memory impairment caused by aging, diseases, flora imbalance and the like can be prevented or alleviated by taking certain probiotics.

It can be seen that adjusting the intestinal flora by the probiotics to further improve the cerebral function and the cognitive competence has become a novel possible way. At the present, the major functions of known probiotics are adjusting intestinal function, improving nutrition metabolism of the host and the like, but there are very few types of known probiotics capable of improving cognitive impairment. Besides, there hasn't been any research so far reporting that certain probiotics can improve the cognitive competence of a healthy individual.

SUMMARY

Technical Problem

At present, the major function of known probiotics is adjusting the intestinal function, and there hasn't been any research reporting that certain probiotics can improve the cognitive competence of a healthy individual. The disclosure is intended to solve the technical problem of screening a probiotic capable of improving the memory of a healthy individual and application thereof.

Technical Solution

In order to solve the technical problem of the disclosure, the disclosure provides *Lactobacillus* sp. BB1 that has been deposited in GDMCC on 25 Mar. 2021, with an accession number: GDMCC No: 61578 and an address: GDIM, 5$^{th}$ Floor, Building No. 59, Yard No. 100, Middle Xianlie Road, Guangzhou.

The disclosure further provides a microbial preparation containing the *Lactobacillus* sp. BB1.

In an embodiment of the disclosure, in the microbial preparation, a viable count of the *Lactobacillus* sp. BB1 is not lower than $1 \times 10^8$ CFU/ml or $1 \times 10^8$ CFU/g.

The disclosure further provides a fermented food capable of improving memory ability of an individual or alleviating memory impairment, where the fermented food contains the *Lactobacillus* sp. BB1 or the microbial preparation.

In an embodiment of the disclosure, in the fermented food, a viable count of the *Lactobacillus* sp. BB1 is not lower than $1 \times 10^8$ CFU/mL or $1 \times 10^8$ CFU/g.

In an embodiment of the disclosure, the fermented food includes a dairy product, a bean product and a fruit and vegetable product or other fermented foods containing the *Lactobacillus* sp. BB1.

In an embodiment of the disclosure, the dairy product includes milk, sour cream and cheese.

In an embodiment of the disclosure, the fruit and vegetable product includes a cucumber product, a carrot product, a beet product, a celery product and a cabbage product, and a product of one or more than two of other edible fruits and vegetables.

In an embodiment of the disclosure, the fermented food further contains an additive selected from one of or a combination of two or more of spice, fruit and vegetable juice, scented tea juice, a colorant, an acidity regulator, a preservative, an antioxidant, a thickener and a sweetening agent.

In an embodiment of the disclosure, the fermented food includes a solid food, a liquid food or a semisolid food in processing form.

The disclosure further provides a feed additive capable of improving memory ability of an individual, where the feed additive contains the *Lactobacillus* sp. BB1 or the microbial preparation.

In an embodiment of the disclosure, in the feed additive, a viable count of the *Lactobacillus* sp. BB1 is not lower than $1 \times 10^8$ CFU/mL or $1 \times 10^8$ CFU/g.

The disclosure further provides application of the *Lactobacillus* sp. BB1 or the microbial preparation in preparing a functional food improving memory ability of an individual or alleviating memory impairment.

In an embodiment of the disclosure, the application is addition of the *Lactobacillus* sp. BB1 or the microbial preparation in a functional food preparation process.

The disclosure further provides application of the *Lactobacillus* sp. BB1 or the microbial preparation in preparing a drug improving memory ability of an individual or alleviating memory impairment.

In an embodiment of the disclosure, the application is addition of the *Lactobacillus* sp. BB1 or the microbial preparation in a drug preparation process.

The disclosure further provides application of the *Lactobacillus* sp. BB1 or the microbial preparation in preparing a probiotic health-care product improving memory ability of an individual or alleviating memory impairment.

In an embodiment of the disclosure, the application is addition of the *Lactobacillus* sp. BB1 or the microbial preparation in a probiotic health-care product preparation process.

Beneficial Effects

In animal experiments of bumblebees and mice, by taking the *Lactobacillus* sp. BB1 provided by the disclosure, the long term memory ability of a health individual can be improved obviously, metabolism of glyceryl phosphatide, amino acids and the like in the intestinal tract can be promoted, a memory beneficial substance glyceryl phosphatide in a blood can be improved, expression of neural receptors in the intestinal tract and the brain can be affected, and transmission of neural signals can be promoted. The fermented food plays the role of remarkably improving the long term memory ability of the individual as well.

The *Lactobacillus* sp. BB1 disclosed by the disclosure can be used for preparing functional foods, health-care products and drugs that enhance and improve the memory ability or alleviate memory impairment, and has a wide application prospect.

Deposit of a Biological Material

A *Lactobacillus* sp. BB1 taxonomically named *Lactobacillus* sp. has been deposited in GDMCC on 25 Mar. 2021, with an accession number: GDMCC NO: 61578 and an address: GDIM, $5^{th}$ Floor, Building No. 59, Yard No. 100, Middle Xianlie Road, Guangzhou.

DETAILED DESCRIPTION

Figure 1A:
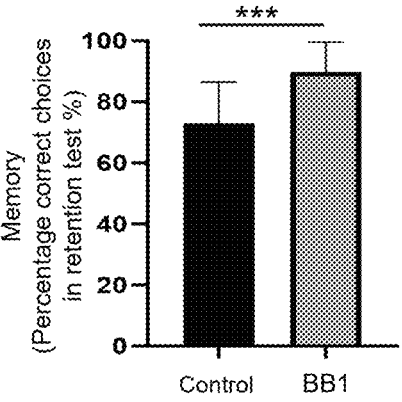
FIG. 1A The *Lactobacillus* sp. BB1 can improve the memory ability of an individual remarkably.

Description on the preferred examples of the disclosure is made below. It is to be understood that the examples are intended to better explain the disclosure rather than limiting the disclosure.

Culture media involved in the examples below are as follows:

An MRS solid culture medium was prepared from 10.00 g/L tryptone, 5.00 g/L yeast extract, 10.00 g/L beef extract, 20.00 g/L glucose, 2.00 g/L triammonium citrate, 5.00 g/L anhydrous sodium acetate, 0.10 g/L magnesium sulfate, 0.05 g/L manganese sulfate, 2.00 g/L dipotassium hydrogen phosphate, 1.00 mL/L tween-80 and 15.00 g/L agar powder, and a pH of the culture medium was adjusted to 6.5.

An MRS liquid culture medium was prepared from 10.00 g/L tryptone, 5.00 g/L yeast extract, 10.00 g/L beef extract, 20.00 g/L glucose, 2.00 g/L triammonium citrate, 5.00 g/L anhydrous sodium acetate, 0.10 g/L magnesium sulfate, 0.05 g/L manganese sulfate, 2.00 g/L dipotassium hydrogen phosphate and 1.00 mL/L tween-80, and a pH of the culture medium was adjusted to 6.5.

Example 1 Strain Screening and Identification (I) Isolation and Screening of *Lactobacillus* sp.
  (1) hindgut tissues of 3 healthy bumblebees were taken and ground to a homogenate; the homogenate was coated to the MRS solid culture medium after being subjected to gradient dilution, and was placed in an anaerobic environment for culture at 37° C. for 72 h;
  (2) a colonial morphology was observed and recorded, and a colony was picked for streaking purification; and
  (3) a single colony was picked, and bacterial cells were collected for strain identification after the single colony was cultured at 37° C. for 48 h in the MRS liquid culture medium.
(II) Molecular Biological Identification of *Lactobacillus* sp.:
  (1) a genome DNA of the single colony was extracted by using an E.Z.N.A. Stool DNA kit (Omega Bio-tek);
  (2) a universal primer was identified by using a bacterial strain to amplify 16S rDNA;
  (3) a 1% agarose gel was prepared, a PCR product and a loading buffer were mixed and then sampled, running was performed at 150 V and 100 mA for 20 min, and observation was performed and the agarose gel was cut;
  (4) the obtained PCR product was delivered to a professional sequencing company for sequencing, search and similarity comparison were made on an obtained sequencing result in a GeneBank database by using BLAST, and it was identified as *Lactobacillus* sp.;
  (5) whole genome sequencing: a whole genome extracted in (1) was delivered to a professional sequencing company, the whole genome of the strain was sequenced by using a second generation sequencer, search and similarity comparison were made on an obtained sequence result in a GeneBank database by using BLAST, and it was identified by the sequencing result that the strain was *Lactobacillus* sp. and was named *Lactobacillus* sp. BB1; and the strain was deposited at −80° C. for later use.

Example 2 Influence of *Lactobacillus* sp. BB1 on Memory Ability of Bumblebees Activated *Lactobacillus* sp. BB1 was subjected to anaerobic culture at 37° C. for 48 h in the MRS liquid culture medium; and *Gilliamella apicola* screened in a same batch was activated and inoculated to an LB liquid culture medium, was cultured in a $CO_2$-enriched (6%) condition at 37° C. for 48 h. A fresh stable phase bacterial culture solution was centrifugalized and washed with PBS, and a bacterial precipitate was dissolved in 40% (w/w) sucrose solution, where a bacterial concentration reached OD600=1.0.

Newly emerged worker bees were marked with number tags every day, they were transferred to different small wooden boxes for different group feeding when they are 3 days old, they were divided into 3 groups, and each group contained 15 worker bees. A specific grouping condition was as follows: (1) a control group: 40% (w/w) sucrose solution was provided every day; (2) a group fed with the *Lactobacillus* sp. BB1: newly prepared 40% sucrose solution containing the *Lactobacillus* sp BB1 (OD$_{600}$=1) every day was provided; (3) a group fed with a control strain *Gilliamella apicola*: newly prepared 40% sucrose solution containing the *G. apicola* (OD$_{600}$=1) every day was provided for feeding for totally 10 days.

Figure 1B:
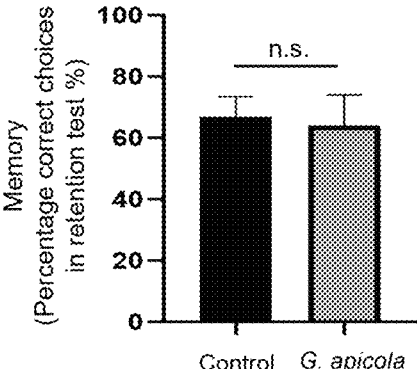
FIG. 1B a control strain *G. apicola* does not affect the memory ability of the individual; ***$P<0.001$.

The bumblebees were put back in the bee colony for learning training when they are 9 days old, and were put back in the bee colony for memory test when they are 12 days old. A specific implementation method and a result were as follows:

Discrimination learning of 10 colors: an individual bumblebee was trained independently to learn to memorize ten colors, where five colors indicate rewards (containing 7 μl of 40% sucrose solution) and the other five colors indicate punishment (containing 7 μl of saturated quinine water). There were two flowers in each color, and there were totally twenty flowers in a flight case. Each bumblebee was trained to fly 5 times at 10-minute flight intervals. At each flight interval, an artificial flower was cleaned and scrubbed with 70% alcohol to make sure no odors or sugar water left to affect the result. On the third day after training, the bumblebees were put back in the bee colony for memory test. Each bumblebee was tested independently. The artificial flowers in the flight arena were placed randomly but were consistent in color with those in training. All the artificial flowers contained deionized water. Color selection of the bumblebee was recorded within three minutes to calculate the long-term memory ability of the bumblebee. The result was as shown in FIG. 1A-B, compared with the control group, by feeding the *Lactobacillus* sp. BB1, the memory ability could be improved remarkably. The selection accuracy of the group fed with the *Lactobacillus* sp. BB1 was about 1.2 times that of the control group. By feeding the control strain *G. apicola*, there was no influence on memory, and the memory ability could not be improved.

Example 3 Influence of *Lactobacillus* sp. BB1 on Metabolism and Content of Glycerophospholipids in Intestinal Tract The bumblebees in the control group and the group fed with the *Lactobacillus* sp. BB1 in Example 2 were placed on dry ice to suffocate them, and hindgut tissues, hemolymphs and brain tissues of the bumblebees were dissected and extracted. Tissue samples were ground with liquid nitrogen respectively and placed in EP tubes, and an 80% methanol aqueous solution containing 0.1% formic acid was added. The tissue samples were left still in an ice bath for 5 min after being subjected to vortex oscillation, and were centrifugalized at 15000 g and 4° C. for 10 min. A certain amount of supernatant was taken, and mass spectrum level water was added to dilute the supernatant till the content of methanol was 53%. The mixture was placed in a centrifuge tube and centrifugalized at 15000 g and 4° C. for 10 min and a supernatant was collected and sampled to LC-MS for analysis.

Figure 2A:
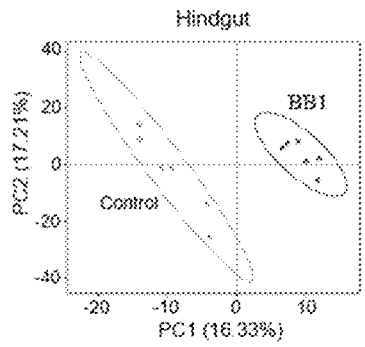
FIG. 2A different metabolites in a hindgut.
Figure 2B:
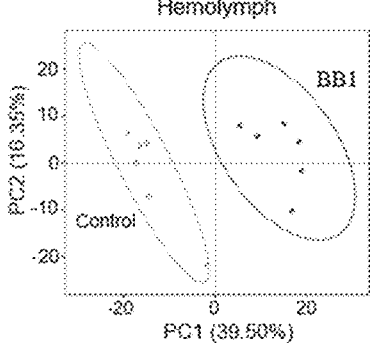
FIG. 2B different metabolites in a hemolymph.
Figure 2C:
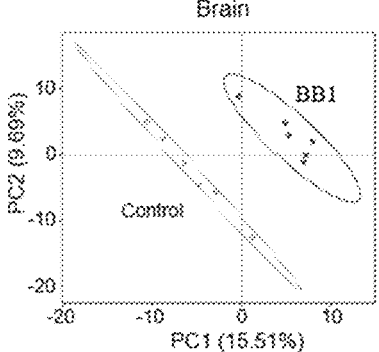
FIG. 2C different metabolites in a brain.
Figure 2D:
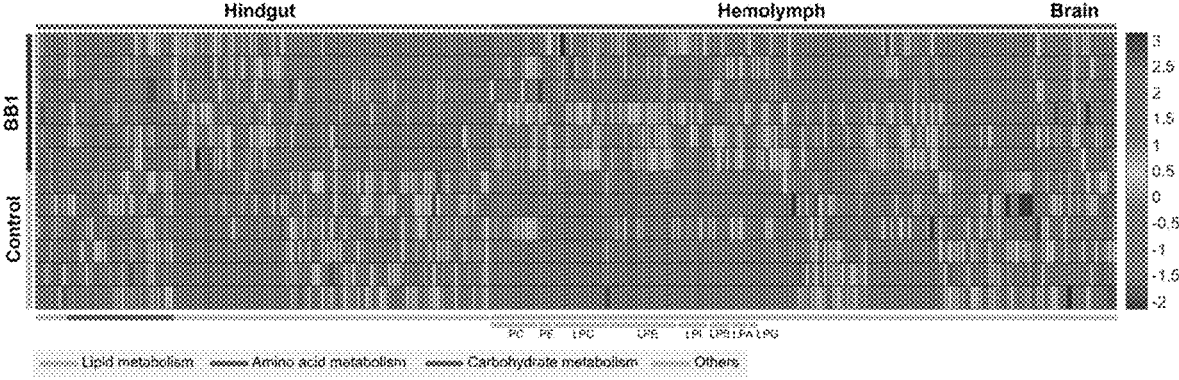
FIG. 2D functions of differential metabolites in different tissues.

A result showed that by feeding the *Lactobacillus* sp. BB1, metabolites in the intestinal tract, hemolymph and brain could be changed remarkably (FIG. 2A-C, a partial least squares discriminant analysis result showed that two groups in different tissues could be differentiated), with differential metabolites being 102, 122 and 19, respectively. The differential metabolites in the intestinal tract mainly took part in lipid metabolism, amino acid metabolism and metabolism of carbohydrates (FIG. 2D), where the metabolites with large content change were key components taking part in synthesizing glycerophospholipids. A result showed that about half of differential metabolites in the hemolymph were glycerophospholipids. Compared with the control group, the *Lactobacillus* sp. BB1 could improve the content of glycerophospholipids in the hemolymph remarkably (FIG. 2D), for example, LPA16.0 was improved by 77 times, and LPE14:1 and LPC18:1 were improved by 13 times.

Example 4 Influence of *Lactobacillus* sp. BB1 on Expression of Neural Receptors in Intestinal Tract and Brain The hindguts and brain tissues of the bumblebees of the control group and the group fed with the *Lactobacillus* sp. BB1 in Example 2 were dissected, total RNA of the hindguts and brain tissues were respectively extracted by using an SV Total RNA Isolation System kit (Promega), cDNA was reversely transcribed by using an iScript™ Advanced cDNA Synthesis Kit (Bio-Rad Laboratories), quantitative real-time PCR was performed by using an iTaq™ Universal SYBR® Green Supermix kit (Bio-Rad Laboratories), and the neural receptors of the hindguts and brain tissues were detected. A housekeeping gene β-Actin was a reference gene, and used primer sequences were shown in a table 1.

TABLE 1

| Quantitative real-time PCR primer sequences | | |
| --- | --- | --- |
| Gene | Forward primer | Reverse primer |
| Actin | TGACGCAGATTATGTT TGAA (SEQ ID NO: 1) | AGCGTATAGCGAAAGTA CAGC (SEQ ID NO: 2) |
| mGlu2 | GGCATTCAAAGATTTG CCGC (SEQ ID NO: 3) | GCTGTGTTTGCTCGCAT TGA (SEQ ID NO: 4) |
| NR2B | CATCCGCTACCGCCAT ACTT (SEQ ID NO: 5) | CGTCGTCCGGAATCCTG TAG (SEQ ID NO: 6) |
| OARO | AAACGGGGGATGAGAT GTCG (SEQ ID NO: 7) | TCGGAATCTTTTCACCT GAGCT (SEQ ID NO: 8) |
| OARβ1 | ACCTCGAGACTCCGAA GATGT (SEQ ID NO: 9) | ACGTTGCACGGTTGCAT TTC (SEQ ID NO: 10) |
| OARβ2 | TCACAGCGTTGAATGT AACCAC (SEQ ID NO: 11) | TCAGAATCGTGTACGGT GGC (SEQ ID NO: 12) |

Figure 3A:
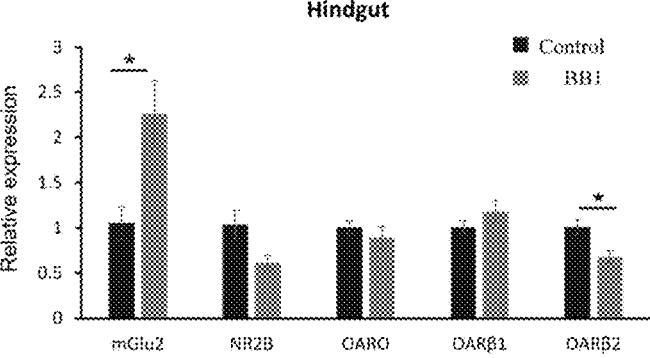
FIG. 3A change of neural receptors in a hindgut; (B) change of neural receptors in a brain; *$P<0.05$, **$P<0.01$.
Figure 3B:
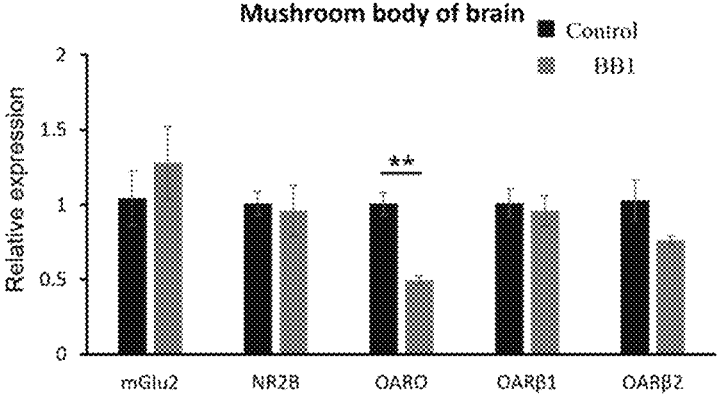
FIG. 3B change of neural receptors in a brain; *$P<0.05$, **$P<0.01$.

A result was shown in FIG. 3A-B. Compared with the control group, expression of glutamate receptors in the intestinal tract of the group fed with the *Lactobacillus* sp. BB1 was improved by 2.1 times, expression of octopamine receptors in the intestinal tract and brain were reduced, the octopamine receptor OARβ2 in the intestinal tract was reduced by 0.7 times, and the octopamine receptor OARO in the brain was reduced by 0.5 times. Signal transmission was affected by affecting expression of neural receptors, so that the memory ability was further affected.

Example 5 Influence of *Lactobacillus* sp. BB1 on Memory Ability of Mouse Individual Influence of *Lactobacillus* sp. BB1 on memory ability of a mouse was evaluated by adopting novel object recognition and a Morris water maze experiment.

Preparation of a bacteria-containing PBS solution: activated *Lactobacillus* sp. BB1 was subjected to anaerobic culture at 37° C. for 48 h in an MRS liquid culture medium. A fresh stable phase bacterial culture solution was centrifugalized and washed with PBS, and a bacterial precipitate was dissolved in the PBS solution, where a bacterial concentration reached $OD_{600}=1.0$.

Two groups of experiments were set: a control group and a *Lactobacillus* sp. BB1 gavage group, respectively, 10 mice in each group. The mice in the control group were gavaged with 0.2 ml of PBS solution every day; and the mice in the *Lactobacillus* sp. BB1 gavage group were gavaged with 0.2 ml of PBS solution containing the *Lactobacillus* sp. BB1 ($OD_{600}=1$) every day for 20 days.

Figure 4A:
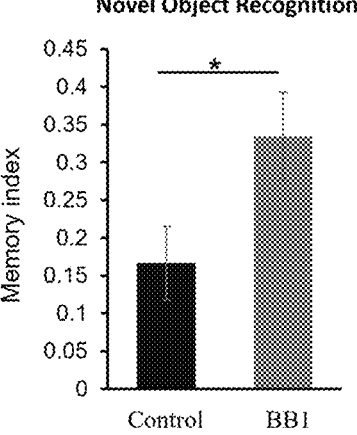
FIG. 4A a novel object recognition capability; (B) the percentage of time spent in a target quadrant in a Morris water maze; (C) the number of crossing platform in the Morris water maze; *$P<0.05$, **$P<0.01$.
Figure 4B:
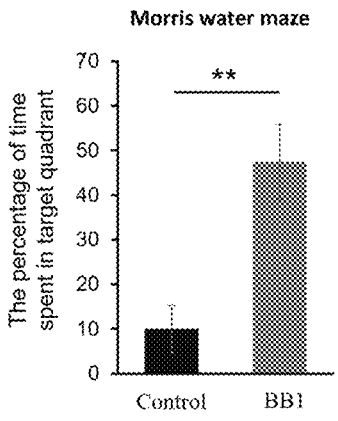
FIG. 4B the percentage of time spent in a target quadrant in a Morris water maze.
Figure 4C:
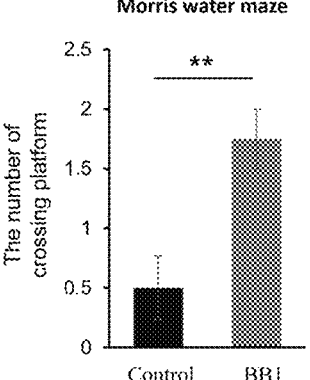
FIG. 4C the number of crossing platform in the Morris water maze; *$P<0.05$, **$P<0.01$.

(1) a novel object recognition experiment: two same objects were placed in a same test box during training, and a tested animal sought for 5 min in the test box; one of the objects was replaced by a novel object after 24 h, then the tested animal was placed in the test box for test for 5 min to investigate whether it could identify that one of the object is the novel object, the time during which the mouse sniffs each object was recorded, and a memory index (memory index=novel object time/(novel object time+old object time)) was evaluated. A result was shown in FIG. 4A-C. The *Lactobacillus* sp. BB1 could improve the memory index of the mouse remarkably, and the memory index was 2.0 times that of the mice in the control group, enhancing the recognition of the mice on the novel object.

(2) a Morris water maze experiment: the experiment lasted 6 days totally, and training was performed 4 times in fixed time periods every day. On the first day, the mice were trained to stand on a platform, on the second day to the fifth day, the mice were placed in a first quadrant, and the mice were placed, facing a pool wall, in a pool from any point of four starting points of the pool wall. A free video recording system recorded time and swimming paths of the mice finding the platform, and in these 4 times of training, the mice were placed in water from different starting points (different quadrants). If the mice could not find the platform within 60 s, they were guided to the platform and had a rest on the platform for 10 s, and next training was then performed at an interval of 1 min. On the sixth day, the platform was removed, the mice were placed in water at the same entry point in a specific quadrant, the swimming paths of the mice within 60 s were recorded, and the number of crossing a target quadrant platform by the mice were recorded.

A result showed that the *Lactobacillus* sp. BB1 could improve the retention time of the mice in the target quadrant remarkably, and improve the number of crossing the platform, which were respectively 4.8 times and 3.5 times that of the control group. It could be seen that the *Lactobacillus* sp. BB1 could enhance the spatial memory ability of the mice remarkably.

Example 6 Application of *Lactobacillus* sp. BB1

Fresh cow milk and white granulated sugar were homogenized (10:1) after being evenly mixed, cooled to 35° C. after being sterilized at 140° C. for 2 s, then a *Lactobacillus* sp. BB1 inoculant leavening agent prepared in the disclosure was inoculated for sealed fermentation at 35° C. for 4 h, then the mixture was transferred to a 4° C. refrigerator and placed for 12 h for post-maturation so as to obtain a final fermented product (a bacterial concentration was $10^8$ CFU/ml or above).

By utilizing the disclosure, other fermented foods can be produced and prepared by fermentation of the *Lactobacillus* sp. BB1. The fermented food includes a solid food, a liquid food and a semisolid food. The fermented food includes a dairy product, a beam product and a fruit and vegetable product. The dairy product includes milk, sour cream and cheese. The fruit and vegetable product includes a cucumber product, a carrot product, a beet product, a celery product and a cabbage product.

Example 7 Application of *Lactobacillus* sp. BB1

A single colony of the *Lactobacillus* sp. BB1 obtained in Example 1 was picked and inoculated to an MRS liquid culture, and was subjected to anaerobic culture at 37° C. for 48 h to obtain a bacterial solution; the bacterial solution was centrifugalized and a precipitate was collected; the precipitate washed by a PBS buffer solution twice was centrifugalized again to obtain bacterial cells; and the bacterial cells of the *Lactobacillus* sp. BB1 was resuspended with a protective agent solution containing 130 g/L skim milk, 20 g/L mycose and 20 g/L saccharose till a cell concentration was $1\times10^8$ CFU/mL, so as to obtain a liquid preparation of the *Lactobacillus* sp. BB1.

The mice were gavaged every day with 0.2 ml of the liquid preparation for continuously 20 days, so that the memory ability of the mice could be improved effectively.

Although disclosed with preferred examples above, the disclosure is not limited by the examples. Any of those skilled in the art may make various alternations and modifications without departing the spirit and scope of the disclosure. Therefore, the scope of protection of the disclosure should be subject to the scope of the disclosure as defined in the claims.

---

What is claimed is:

1. A composition, comprising:

i) an anaerobic culture of *Lactobacillus* sp. BB1 with accession number GDMCC 61578, wherein the anaerobic culture is at 37° C. for 48 hour, ii) skim milk, mycose (trehalose), and saccharose (sucrose), and iii) a dairy product, a bean product, or a fruit and vegetable product, wherein the dairy product is selected from the group consisting of sour cream and cheese, and wherein the fruit and vegetable product comprises cucumber, carrot, beet, celery, cabbage, or a combination thereof.

2. The composition according to claim 1, wherein a viable count of the *Lactobacillus* sp. BB1 is not lower than $1 \times 10^8$ CFU/mL or $1 \times 10^8$ CFU/g.

3. The composition according to claim 1, wherein the composition is liquid or semisolid.

4. A feed additive comprising or comprised of the composition of claim 1.

5. The feed additive according to claim 4, wherein a viable count of the *Lactobacillus* sp. BB1 is not lower than $1 \times 10^8$ CFU/mL or $1 \times 10^8$ CFU/g.

6. A drug, food, or health-care product prepared by a process, which comprises adding to the drug, food, or health-care product an anaerobic culture of *Lactobacillus* sp. BB1 with accession number GDMCC 61578, wherein the anaerobic culture is at 37° C. for 48 hours.

*    *    *    *    *